United States Patent

Kuwahara et al.

Patent Number: 5,068,453
Date of Patent: Nov. 26, 1991

[54] NOVEL MONOTERPENES

[75] Inventors: Yasumasa Kuwahara; Walter S. Leal, both of Ibaraki, Japan

[73] Assignee: Daikin Industries, Ltd., Osaka, Japan

[21] Appl. No.: 491,459

[22] Filed: Mar. 9, 1990

[30] Foreign Application Priority Data

Mar. 13, 1989 [JP] Japan .................................. 1-60324
Apr. 28, 1989 [JP] Japan ................................. 1-109938

[51] Int. Cl.$^5$ ............................................. C07C 47/21
[52] U.S. Cl. ..................................................... 568/494
[58] Field of Search ........................................ 568/494

[56] References Cited

U.S. PATENT DOCUMENTS

Re. 28,263 12/1974 Gauvreau .

OTHER PUBLICATIONS

Larcheveque et al., Tet. Lett., 22(17), 1595–8 (1981).
Poulter et al. (1981) Journal of Organic Chemistry, 46:1532–1538.

Primary Examiner—Nicky Chan
Attorney, Agent, or Firm—Birch, Stewart, Kolasch & Birch

[57] ABSTRACT

Monoterpenes of the formulae:

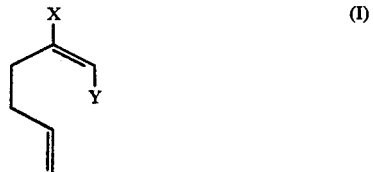

and

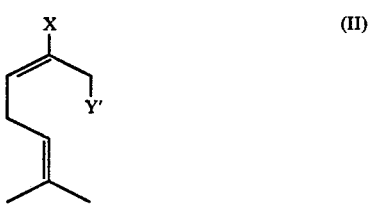

wherein X, Y and Y' are independently —CHO, —CO$_2$H or —CH$_2$OR, R being hydrogen or tetrahydropyranyl, and Y may be in E- or Z-form about the adjacent double bond have been isolated from agriculturally harmful acarids and then identified. They have fragrance of citrus-note and are bactericidally active against bacteria which may cause crop injury. Some of them are the first sex pheromones to be isolated from the acarids.

3 Claims, No Drawings

NOVEL MONOTERPENES

BACKGROUND OF THE INVENTION

Field of the Invention

The present invention relates to novel monoterpenes.

Description of the Related Art

Monoterpenes are hydrocarbons having a basal structure of $C_{10}H_{16}$. Most of them are naturally found in essential oils. The monoterpenes have been utilized, for example, in an insecticide, medicine or perfume due to their volatility and fragrance.

SUMMARY OF THE INVENTION

Novel monoterpenes have been isolated from agriculturally harmful acarids and then identified. They have fragrance of citrus-note and are bactericidally active against bacteria which may cause crop injury. Some of them are the first sex pheromones to be isolated from the acarids.

Accordingly, the present invention provides monoterpenes of the formulae:

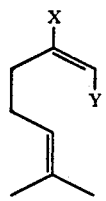
(I)

and

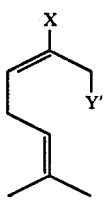
(II)

wherein X, Y and Y' are independently —CHO, —CO$_2$H or —CH$_2$OR, R being hydrogen or tetrahydropyranyl, and Y may be in E- or Z-form about the adjacent double bond.

DETAILED DESCRIPTION OF THE INVENTION

The monoterpenes of the formula (I) can be obtained from an acarid named Tyrophagus perniciosus.

Other acarids such as Tyrophagus putrescentiae and Caloglyphus polyphyllae give the monoterpenes of the formula (II).

The present monoterpenes (I) and (II) have fragrance of citrus-note and bactericidal activity against some bacteria which may harm crops.

In addition, the monoterpenes (II) are the first sex pheromones that have been isolated from genus acarid, which attract male Caloglyphus polyphyllae. Therefore, it is possible to use the monoterpenes (II) as an attractant.

Specific examples of the present monoterpenes as well as their characteristic data are shown as follows:

2-(4-methyl-3-pentenyl)-2-butenedial (hereinafter referred to as α-acaridial):

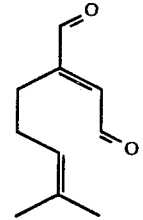

MS: 166.0983 (M+)
IR (CCl$_4$): 1690 cm$^{-1}$
UV (hexane): $\lambda_{max}$=240 nm, $\epsilon$=23500
NMR (500 MHz, CDCl$_3$): $\delta$=9.67 (s), 10.17 (d, J=7.54 Hz), 6.51 (d, J=7.54 Hz), 5.07 (triplet-quintet, J=7.74, 7.64, 1.5 ppm), 2.71 (t, J=7.14 Hz), 2.19 (q, J=7.4 Hz), 1.65 (3H, s), 1.50 (2H, s).

2-(4-methyl-3-pentenyl)-2(E)-butenediol [hereinafter referred to as α-(E)-acaridiol]:

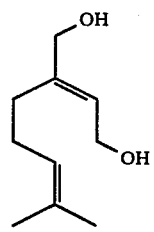

NMR (500 MHz, CDCl$_3$) $\delta$=5.69 (1H, t, J=6.85 Hz), 5.11 (1H, m), 4.21 (2H, d, J=6.85 Hz), 4.09 (2H, s), 2.05–2.20 (4H, m), 1.69 (3H, s), 1.61 (3H, s).
$^{13}$C-NMR: $\delta$=142.34, 132.76, 124.72, 123.57, 66.38, 58.88, 28.24, 27.19, 25.68, 17.75.

2-(4-methyl-3-pentenyl)-2(Z)-butenediol [hereinafter referred to as α-(Z)-acaridiol]:

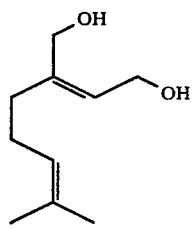

NMR (500 MHz, CDCl$_3$): $\delta$=5.64 (1H, t, J=6.87 Hz), 5.11 (1H, m), 4.21 (2H, d, J=6.87), 4.18 (2H, s), 2.02–2.20 (4H, m), 1.69 (3H, s), 1.61 (3H, s).
$^{13}$C-NMR: $\delta$=143.71, 132.22, 126.75, 123.68, 61.05, 58.83, 35.82, 26.71, 25.68, 17.75.

2(E)-(4-methyl-3-pentenylidene)-butanedial (hereinafter referred to as β-acaridial):

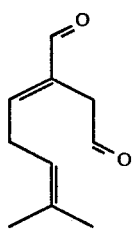

MS: 166.0988 (M+), M/Z =151, 137, 123
IR (CCl$_4$): 2810, 2700, 1720, 1680 cm$^{-1}$

UV (hexane): $\lambda_{max} = 225$ nm, $\epsilon = 13600$

NMR (500 MHz, CDCl$_3$): $\delta = 9.45$ (s), 9.62 (t, J=1.6 Hz), 6.75 (t, J=7.44 Hz), 5.12 (triplet-quintet, J=7.25, 7.1, 1.28 Hz), 3.43 (2H, d, J=1.3 Hz), 3.00 (2H, t, J=7.34 Hz), 1.73 (3H, s), 1.65 (3H, s).

2(E)-(4-methyl-3-pentenylidene)-butanediol (hereinafter referred to as β-acaridiol):

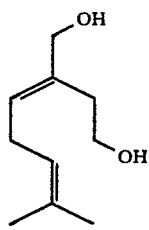

$^{13}$C-NMR: $\delta = 135.97$ (C), 132.47 (C), 130.02 (CH), 121.99 (CH), 61.80 (CH$_2$), 58.45 (CH$_2$), 32.38 (CH$_2$), 26.82 (CH$_2$), 25.67 (CH$_3$), 17.77 (CH$_3$).

The present monoterpenes can be obtained as follows by the isolation from the acarids or the synthesis:

Isolation from acarids:

Tyrophagus perniciosus was cultured and extracted with n-hexane. The extract was subjected to silica column chromatography eluted with n-hexane/ether. α-Acaridial was obtained in fractions of 95:5–90:10.

By the same way, β-acaridial was isolated from Tyrophagus putrescentiae in the fractions of 90:10–80:20.

Synthesis:

The present monoterpenes (I) can be obtained according to the following reaction formulae:

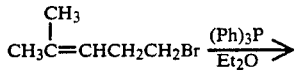

TOCH$_2$COCH$_2$CH$_2$OT (T: 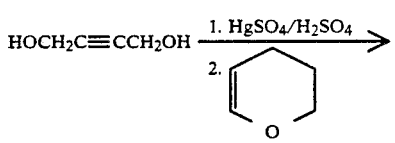 )

TOCH$_2$COCH$_2$CH$_2$OT + CH$_3$C(CH$_3$)=CHCH$_2$CH$_2$Br $\xrightarrow{\text{Mg/Et}_2\text{O}}$

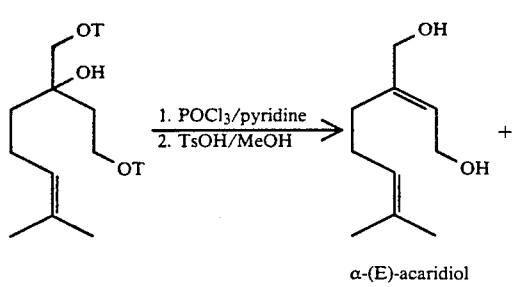

α-(E)-acaridiol

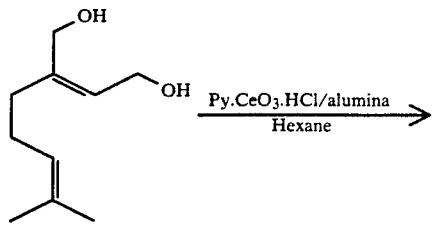

α-(Z)-acaridiol

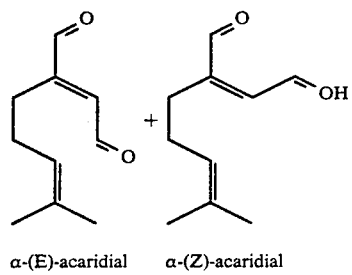

α-(E)-acaridial    α-(Z)-acaridial

The present compounds (II) may be prepared as follows:

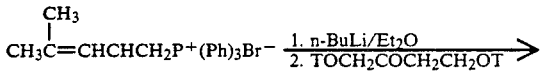

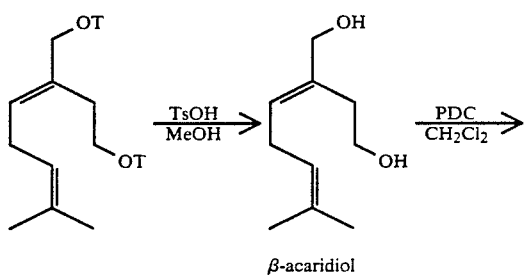

β-acaridiol

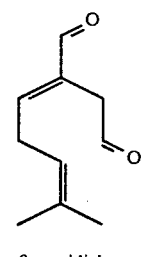

β-acaridial

PREFERRED EMBODIMENTS OF THE INVENTION

EXAMPLE 1

Bactericidal activity of α-acaridial and β-acaridial

By using a paper disc for antibiotics assay (diameter: 8 cm), the bactericidal activity of α-acaridial and β-acaridial was examined against the bacteria shown in Tables 1 and 2.

In the examination, a usual agar medium was used as a culture medium for the bacteria. A solution of the test compound in ethanol was applied on the disc so as to inhibit the bacteria. The bactericidal activity was determined as a diameter of the inhibited area.

The results as well as the concentration of the ethanol solution of the test compounds are shown in Tables 1 and 2.

TABLE 1

Bactericidal activity of α-acaridial

| Concentration | Inhibition diameter (mm) | | |
|---|---|---|---|
| (μm/ml) | A | P | F |
| 1000 | 9 | 15.8 | 13.6 |
| 500 | 8 | 13.6 | 11.7 |
| 250 | — | 12.0 | 10.1 |
| 125 | — | 10.3 | 8.5 |

TABLE 2

Bactericidal activity of β-acaridial

| Concentration | Inhibition diameter (mm) | | |
|---|---|---|---|
| (μm/ml) | A | P | F |
| 500 | 8.0 | 14.3 | 11.5 |
| 400 | — | 12.0 | 10.3 |
| 320 | — | 11.6 | 9.7 |
| 256 | — | 11.1 | 9.5 |
| 205 | — | 11.1 | 8.8 |
| 164 | — | 9.6 | 8.6 |
| 131 | — | 9.4 | 8.4 |
| 105 | — | 9.3 | 8.0 |
| 84 | — | 8.0 | — |

A: Alternaria alternata
P: Penicillium Vermicalatum IFO 7231
F: Fusarium Oxysporum

EXAMPLE 2

Attraction of β-acaridial for male Caloglyphus polyphyllae

Into a dish (diameter: 4 cm) containing a small amount of dry yeast on the center thereof and a moist piece of filter paper placed aside from the center, ten head of male Caloglyphus polyphyllae were introduced. The moment the acarids began to eat the yeast, two pieces of filter paper were put on the dish symmetrically about the center, one piece containing a solution of the test compound and the other piece only a solvent as a control. The distance between the center of the dish and each piece was 1 cm. The attraction was concluded to be positive when the acarid stopped to eat and moved or were headed toward the test piece.

The positive attraction was achieved with the minimal concentration of β-acaridial of 1 ppm, which is about a half of the β-acaridial concentration in one head of female Caloglyphus polyphyllae.

What is claimed is:

1. A monoterpene of the formula:

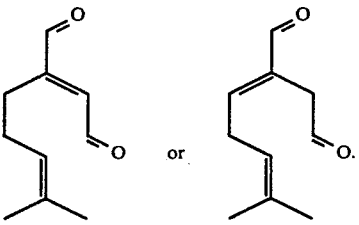

2. A monoterpene of the formula:

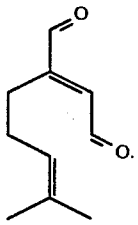

3. A monoterpene of the formula:

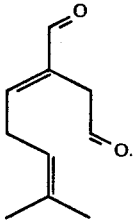

* * * * *